United States Patent
Xie et al.

(10) Patent No.: US 10,054,434 B2
(45) Date of Patent: Aug. 21, 2018

(54) SURFACE ROUGHNESS MEASUREMENT DEVICE

(71) Applicant: General Electric Company, Schenectady, NY (US)

(72) Inventors: Guangping Xie, Shanghai (CN); Ming Jia, Shanghai (CN); Zirong Zhai, Shanghai (CN); Paolo Trallori, Florence (IT); Kevin George Harding, Niskayuna, NY (US); Guiju Song, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 234 days.

(21) Appl. No.: 14/787,134

(22) PCT Filed: Apr. 25, 2014

(86) PCT No.: PCT/US2014/035407
§ 371 (c)(1),
(2) Date: Oct. 26, 2015

(87) PCT Pub. No.: WO2014/176479
PCT Pub. Date: Oct. 30, 2014

(65) Prior Publication Data
US 2016/0069672 A1    Mar. 10, 2016

(30) Foreign Application Priority Data

Apr. 26, 2013  (CN) .......................... 2013 1 0150620

(51) Int. Cl.
*G01B 11/30*    (2006.01)
*G01N 21/47*    (2006.01)
(Continued)

(52) U.S. Cl.
CPC ............ *G01B 11/303* (2013.01); *G01B 11/24* (2013.01); *G01B 11/30* (2013.01); *G01B 11/306* (2013.01); *G01N 21/47* (2013.01); *G01N 21/55* (2013.01)

(58) Field of Classification Search
CPC ....... G01B 11/24; G01B 11/30; G01B 11/303; G01B 11/306; G01N 21/47; G01N 21/55
See application file for complete search history.

(56) References Cited

U.S. PATENT DOCUMENTS 4,146,330 A * 3/1979 Belden, Jr. ........... G01B 11/303
356/445
4,634,879 A   1/1987 Penney
(Continued)

FOREIGN PATENT DOCUMENTS

CN   2427793 Y   4/2001
CN   1414377 A   4/2003
(Continued)

OTHER PUBLICATIONS

Vorburger et al., "Surface Roughness Studies with Dallas-Detector Array for Laser Light Angular Scattering", Journal of Research of the National Bureau of Standards, vol. No. 89, Issue No. 1, pp. 1-14, 1984.
(Continued)

*Primary Examiner* — Hina F Ayub
*Assistant Examiner* — Amanda Merlino
(74) *Attorney, Agent, or Firm* — GE Global Patent Operation

(57) ABSTRACT

A surface roughness measurement device that in one embodiment includes main and auxiliary emitting fibers, multiple collecting fibers, an optical housing, main and auxiliary reflective mirrors, and an external circuit. The optical housing includes the fibers and defines an aperture
(Continued)

for optically contacting a surface of an object. The main reflective mirror is arranged in the optical housing, for reflecting light emitted from the main emitting fiber to a detecting point of the aperture and reflected light by the object to the collecting fibers. The auxiliary reflective mirror is arranged in the optical housing, for reflecting light emitted from the auxiliary emitting fiber to the detecting point. The external circuit is for generating a laser beam to the main and auxiliary emitting fibers, collecting the reflected light from the collecting fibers, and calculating the surface roughness of the object based on the collected reflected light.

20 Claims, 13 Drawing Sheets

(51) Int. Cl.
*G01N 21/55* (2014.01)
*G01B 11/24* (2006.01)

(56) References Cited

U.S. PATENT DOCUMENTS

| | | | |
|---|---|---|---|
| 4,673,818 A | 6/1987 | Guerra | |
| 4,902,888 A | 2/1990 | Kondo | |
| 5,068,541 A | 11/1991 | Kondo | |
| 6,222,628 B1 | 4/2001 | Corallo et al. | |
| 7,268,871 B2* | 9/2007 | Brown | G01N 21/474 356/301 |
| 7,391,518 B1* | 6/2008 | Schwarz | G01B 11/30 356/445 |
| 7,679,756 B2* | 3/2010 | Sperling | G01J 3/504 356/446 |
| 2003/0090669 A1 | 5/2003 | Jung et al. | |
| 2004/0117052 A1 | 6/2004 | Geng | |
| 2007/0153285 A1 | 7/2007 | Elton et al. | |
| 2008/0294002 A1 | 11/2008 | Xie | |
| 2010/0042084 A1 | 2/2010 | Nariyuki et al. | |
| 2014/0009762 A1* | 1/2014 | Smith | G01N 21/55 356/445 |

FOREIGN PATENT DOCUMENTS

| | | |
|---|---|---|
| CN | 201589600 U | 9/2010 |
| CN | 202533048 U | 11/2012 |
| EP | 1963781 B1 | 6/2010 |
| EP | 2118617 B1 | 9/2010 |
| JP | 62195512 A | 8/1987 |
| JP | 63255607 A | 10/1988 |
| JP | 3181808 A | 8/1991 |
| JP | 0783641 A | 3/1995 |
| JP | 2008032675 A | 2/2008 |

OTHER PUBLICATIONS

Lee et al., "An In-Process Measurement Technique Using Laser for Non-Contact Monitoring of Surface Roughness and form Accuracy of Ground Surfaces", CIRP Annals—Manufacturing Technology Elsevier, vol. No. 36, Issue No. 1, pp. 425-428, 1987.

Liu et al., "A Reflective Fiber Optic Sensor for Surface Roughness In-Process", Journal of Manufacturing Science and Engineering, vol. No. 124, pp. 515-522, Aug. 2002.

Tay et al., "In Situ Surface Roughness Measurement Using a Laser Scattering Method", Optics communication Elsevier, vol. No. 218, Issue No. 1-3, pp. 1-10, Mar. 15, 2003.

PCT Search Report and Written Opinion issued in connection with corresponding Application No. PCT/US2014/035407 dated Aug. 18, 2014.

Unofficial English Translation of Chinese Office Action issued in connection with corresponding CN Application No. 201310150620.9 dated Mar. 8, 2017.

First Office Action and Search issued in connection with corresponding CN Application No. 201480023764.0 dated May 4, 2017.

\* cited by examiner

SURFACE ROUGHNESS MEASUREMENT DEVICE

BACKGROUND

Embodiments of the present disclosure relate generally to surface roughness measurement devices and more particularly to surface roughness measurement devices which can make measurements in difficult access areas and harsh environments.

Surface quality and finish play an important role in areas such as mechanical, optical, and medical, as well as in manufactured goods and electronic devices. Since roughness is such an important characteristic of a component that it is typically subject to quality assurance processes. In certain examples, the surface roughness control dictates the type of manufacturing process and can even affect the functional performance of the component. Therefore, a number of surface roughness measurement methods have been developed in the industry. These methods can be generally classified into two categories, i.e. contact measurement methods and non-contact measurement methods. Typically, most of the surface roughness measurement methods are for the outer surface, and there are a number of known techniques in the industry.

Inner surface roughness measurements tend to be more difficult, especially for smaller size components or components with narrow slots or openings. In addition to inner surface measurements, there are other situations that are not well suited for roughness measurements. For example, a component may have a complex geometry with a non-planar surface that makes surface measurements difficult.

Conventional techniques for difficult surface roughness measurements tend to have drawbacks such as being destructive, having a high cost and time-consuming in a manufacturing environment. Furthermore, the conventional roughness measuring techniques typically cannot easily distinguish the machining mark direction of the object to be measured, and the conventional roughness measurement techniques may not eliminate some parameter variation influence, such as material reflectivity variation, vibration in the shop, and so on.

For these and other reasons, there is a need for providing a surface roughness measurement device particularly for measuring the surface in difficult access areas and providing a precise surface roughness value.

BRIEF DESCRIPTION

In accordance with an embodiment of the present device, a surface roughness measurement device is provided. The surface roughness measurement device in one embodiment includes a fiber bundle including a main emitting fiber, multiple collecting fibers, an auxiliary emitting fiber, an optical housing, a main reflective mirror, an auxiliary reflective mirror, and an external circuit. The optical housing includes the fiber bundle and the auxiliary emitting fiber and defines an aperture for optically contacting a surface of an object. The main reflective mirror is arranged in the optical housing, and used for reflecting light emitted from the main emitting fiber to a detecting point of the aperture and reflecting light reflected by the object to the multiple collecting fibers. The auxiliary reflective mirror is arranged in the optical housing, and used for reflecting light emitted from the auxiliary emitting fiber to the detecting point of the aperture. The external circuit is used for generating a laser beam to the main emitting fiber and the auxiliary emitting fiber, collecting the reflected lights from the multiple collecting fibers, and calculating the surface roughness of the object based on the collected reflected light.

In accordance with another embodiment, a surface roughness measurement device is provided. The surface roughness measurement device includes a fiber bundle including a main emitting fiber, multiple collecting fibers, multiple auxiliary emitting fibers, an optical housing, a main reflective mirror, multiple auxiliary reflective mirrors, and an external circuit. The optical housing includes the fiber bundle and the auxiliary emitting fibers and defines an aperture for optically contacting a surface of an object. The main reflective mirror is arranged in the optical housing, and used for reflecting light emitted from the main emitting fiber to a detecting point of the aperture and reflecting light reflected by the object to the multiple collecting fibers. The auxiliary reflective mirrors are arranged in the optical housing, and used for respectively reflecting light emitted from the auxiliary emitting fibers to the detecting point of the aperture. The external circuit is used for generating a laser beam to the main emitting fiber and the auxiliary emitting fibers, collecting the reflected lights from the multiple collecting fibers, and calculating the surface roughness of the object based on the collected reflected light.

DRAWINGS

These and other features, aspects, and advantages of the present invention will become better understood when the following detailed description is read with reference to the accompanying drawings in which like characters represent like parts throughout the drawings, wherein:

FIG. 9b shows four intensity images representing four surface roughness values calculated by the surface roughness measurement device of FIG. 9a.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Unless defined otherwise, technical and scientific terms used herein have the same meaning as is commonly understood by one of ordinary skill in the art to which this invention belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items, and terms such as "front", "back", "bottom", and/or "top", unless otherwise noted, are merely used for convenience of description, and are not limited to any one position or spatial orientation. Moreover, the terms "coupled" and "connected" are not intended to distinguish between a direct or indirect coupling/connection between two components. Rather, such components may be directly or indirectly coupled/connected unless otherwise indicated.

Figure 1:
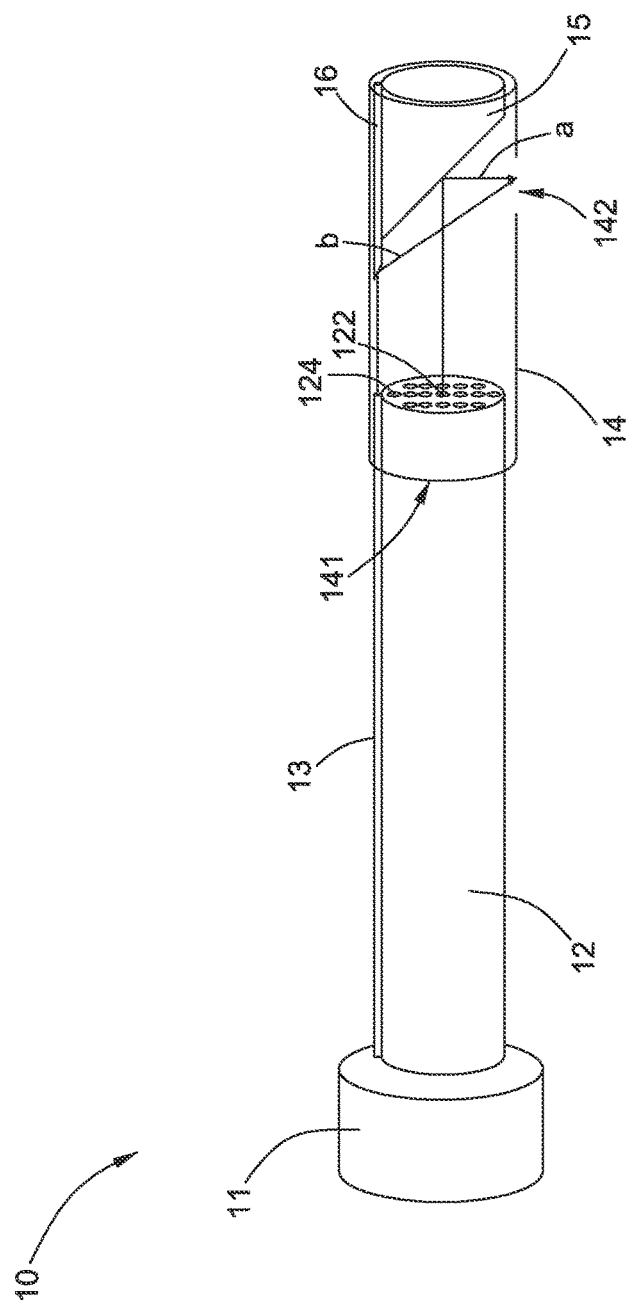
FIG. 1 is a schematic, perspective view of a surface roughness measurement device, according to one embodiment.

Referring to FIG. 1, a schematic view of a surface roughness measurement device 10 according to one embodiment is shown. The surface roughness measurement device 10 includes a cable adapter 11, a fiber bundle 12, an auxiliary emitting fiber 13, an optical housing 14, a main reflective mirror 15, and a miniature auxiliary reflective mirror 16. For ease of showing the arrangement of the elements arranged in the optical housing 14 in the drawings, the optical housing 14 is shown as a transparent type in FIGS. 1, 2, 4a, 4b, and 10, but in one embodiment the optical housing 14 is opaque. For example, the optical housing 14 is made of stainless steel in one embodiment.

Figure 3:
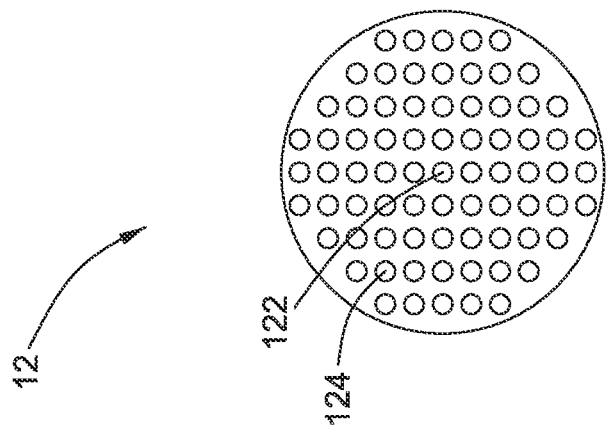
FIG. 3 is a cross-sectional view of a fiber bundle of the surface roughness measurement device of FIG. 1, according to one embodiment.

In some embodiments, the cable adapter 11 is used for providing a communication interface between the fibers in the fiber bundle 12 and external circuits, and between the auxiliary emitting fiber 13 and the external circuits (will described in the latter paragraphs). In one embodiment the fiber bundle 12 includes a main emitting fiber 122 arranged about the center of the fiber bundle 12 and multiple collecting fibers 124 arranged around the main emitting fiber 122. For ease of explaining the arrangement of the fiber bundle 12, only a few collecting fibers 124 are shown in FIG. 1, but there may be more collecting fibers 124 arranged in the fiber bundle 12 (see FIG. 3). The number of the collecting fibers 124 may vary according to design requirements and criteria. For example, the number of the collecting fibers 124 may be one hundred and twenty-six in one embodiment. In this example the fibers 122, 124 of the fiber bundle 12 are arranged within a fiber bundle housing that helps to maintain the fiber position.

The auxiliary emitting fiber 13 is arranged proximate the fiber bundle 12 and has the same emitting direction as the main emitting fiber 122. In one embodiment the auxiliary emitting fiber 13 is coupled to the fiber bundle 12 while in other embodiments, the auxiliary emitting fiber 13 is arranged in the fiber bundle 12 as one of the fibers therein. For measuring surface roughness of an object in difficult access areas, the diameter of the fiber bundle 12 is designed to a small size. For example, in one embodiment the diameter of the fiber bundle 12 is about 2.1 mm, and the combined number of the fibers 122 and 124 of the fiber bundle 12 is one hundred and twenty-seven.

Figure 2:
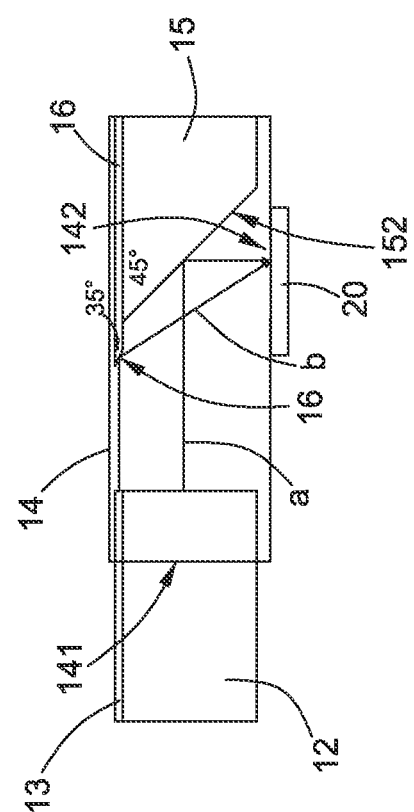
FIG. 2 is a schematic, partial view of the surface roughness measurement device of FIG. 1, together with an object to be measured.

Referring to FIG. 1 and FIG. 2 together, FIG. 2 is a schematic, partial view of the surface roughness measurement device 10 of FIG. 1, together with an object 20 to be measured. In some embodiments, the optical housing 14 is a housing configured to engage the fiber bundle 12 and defining an opening 141 at one end thereof. The distal end of the fiber bundle 12 with the auxiliary emitting fiber 13 is retained in at least part of the optical housing 14 through the opening 141. In one embodiment, the diameter of the optical housing 14 is about 3.0 mm. The main reflective mirror 15 is arranged in the optical housing 14 and optically coupled to the fiber bundle 12 and in one embodiment the main reflective mirror 15 is positioned with respect to the fiber bundle 12 such that the light from the main emitting fiber 122 of the fiber bundle 12 strikes the mirror 15 and is reflected onto the object 20. In one example the main reflective mirror 15 is oriented at approximately 45 degrees with respect to the light from the main emitting fiber 122 of the fiber bundle 12. The reflection area of the main reflective mirror 15 is equal to or bigger than the cross-sectional area of the fiber bundle 12 in some embodiments, which ensures the collecting fibers 124 can collect sufficient reflected light from the main reflective mirror 15 to calculate the roughness of the object 20 in subsequent data processing.

The auxiliary reflective mirror 16 is arranged in the optical housing 14 and is positioned with respect to the auxiliary emitting fiber 13, and in one example the auxiliary reflective mirror is oriented with a gradient angle which is less than 45 degrees, such as 25-35 degrees to the auxiliary emitting fiber 13. In this illustrated example the distance between the auxiliary emitting fiber 13 and the auxiliary reflective mirror 16 is less than the distance between the fiber bundle 12 and the main reflective mirror 15.

The optical housing 14 also defines an aperture 142 below the reflection surface of the main reflective mirror 15. In other words, when a laser beam 'a' is emitted from the main emitting fiber 122 to the main reflective mirror 15, the reflected laser beam 'a' reflected by the main reflective mirror 15 will be transmitted approximately perpendicular to the aperture 142. Furthermore, the arrangement of the auxiliary reflective mirror 16 is oriented such that when a laser beam 'b' is emitted from the auxiliary emitting fiber 13 to the auxiliary reflective mirror 16, the reflected laser beam 'b' reflected by the auxiliary reflective mirror 16 will intersect with the reflected laser beam 'a' reflected by the main reflective mirror 15 at about the same detecting point of the aperture 142.

Namely, when the object 20 is proximate the aperture 142, the reflected laser beams 'a' and 'b' are respectively transmitted to a same detecting point at the measuring surface of the object 20. The gradient angle of the auxiliary reflective mirror 16 can be changed according to the real position arrangement of the auxiliary reflective mirror 16 in the optical housing 14. Because the size of the optical housing 14 is typically small (such as only 3.0 mm), the optical housing 14 can access some difficult access areas, such as inner holes and small grooves, of the object 20 and can measure the surface roughness. In other embodiments, the geometry design of the optical housing 14, the fiber bundle 12, the main reflective mirror 15, and the auxiliary reflective mirror 16 may vary according to different design requirements and criteria.

Referring again to FIG. 3, there are a plurality of optical fibers positioned within the fiber bundle housing, and as depicted, the main emitting fiber 122 is centrally located and has collecting fibers 124 surrounding the main emitting fiber 122. It should be understood that the main emitting fiber 122 can be one or more fibers. The fibers of the fiber bundle 12 are depicted as arranged in a row and column format, however in other embodiments the fibers can be arranged in other formats.

Figure 4A:
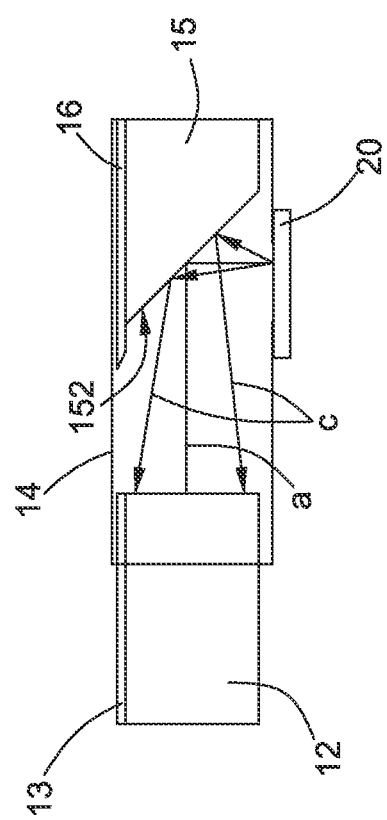
FIG. 4a is a schematic view for showing reflected light from a main emitting fiber of the fiber bundle of the surface roughness measurement device of FIG. 1.

Referring to FIG. 4a, a schematic view for showing reflected light 'c' from the main emitting fiber 122 and reflected by the main reflective mirror 15, the object 20, and the main reflective mirror 15 respectively. FIG. 4a only shows two beams of the reflected light 'c'. Typically, the number of the beams of the reflected light 'c' is typically determined by the roughness of the object 20. When the roughness of the object 20 is high, the number of the beams of the reflected light 'c' becomes larger. In contrast, when the roughness of the object 20 is low, the number of the beams of the reflected light 'c' becomes smaller. The multiple collecting fibers 124 are used to collect the reflected light 'c' for subsequent data processing.

Figure 4B:
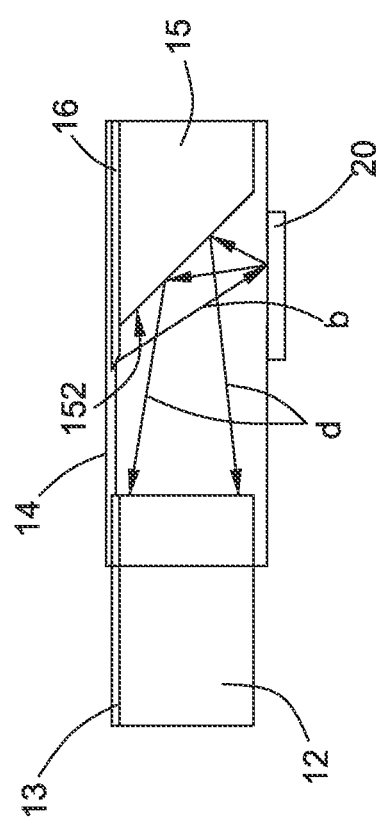
FIG. 4b is a schematic view for showing reflected light from an auxiliary emitting fiber of the surface roughness measurement device of FIG. 1.

Referring to FIG. 4b, a schematic view for showing reflected light 'd' from the auxiliary emitting fiber 13 and reflected by the auxiliary reflective mirror 16, the object 20, and the main reflective mirror 15 respectively. FIG. 4b only shows two beams of the reflected light 'd'. Typically, the number of the beams of the reflected light 'd' is determined by the roughness of the object 20. When the roughness of the object 20 is high, the number of the beams of the reflected light 'd' becomes larger. In contrast, when the roughness of the object 20 is low, the number of the beams of the reflected light 'd' becomes smaller. The multiple collecting fibers 124 are used to collect the reflected light 'd' for subsequent data processing.

Figure 5A:
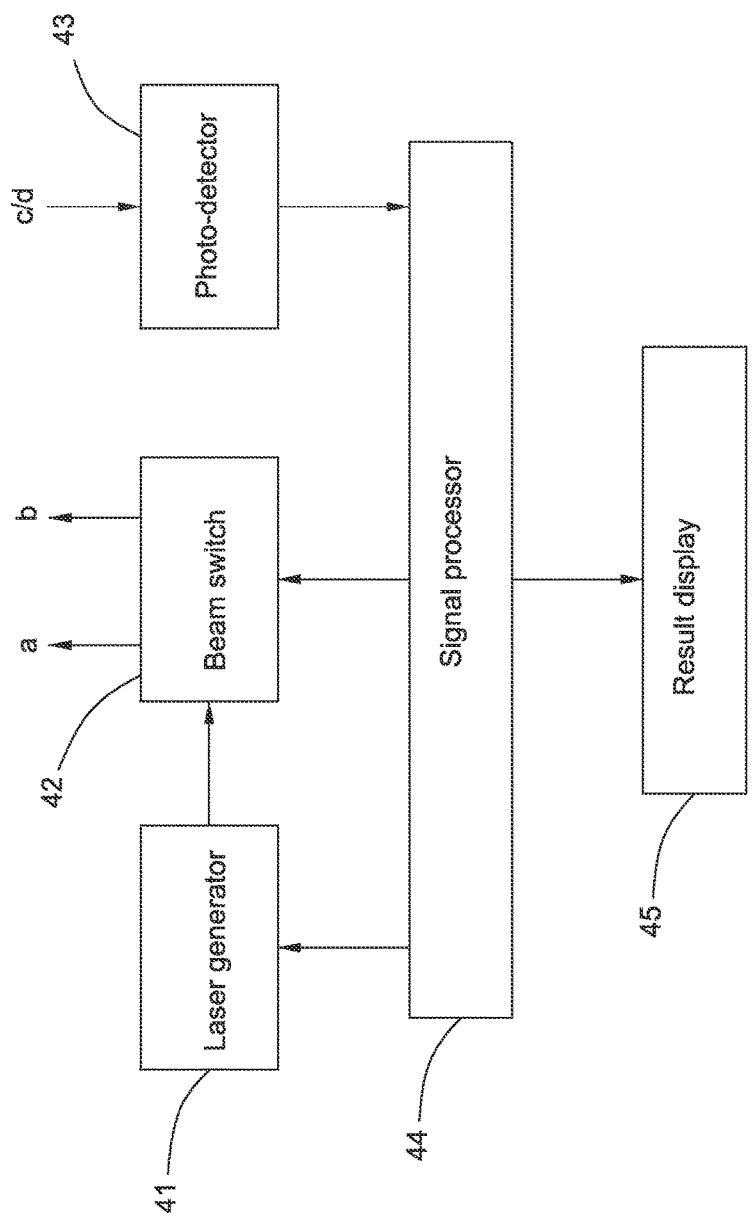
FIG. 5a is a block diagram of the surface roughness measurement device of FIG. 1, according to one embodiment.

Referring to FIG. 5a, a block diagram for the external circuits of the surface roughness measurement device 10 of FIG. 1, according to one embodiment is shown. The external circuits in one example include a laser generator 41, a beam switch 42, a photo-detector 43, a signal processor 44, and a result display 45.

According to one embodiment, the laser generator 41 is used to generate a laser beam according to a drive signal from the signal processor 44. The beam switch 42 is used to collect the laser beam from the laser generator 41 and switch the laser beam to be the laser beam 'a' emitted from the main emitting fiber 122 or the laser beam 'b' emitted from the auxiliary emitting fiber 13 according to a switch signal from the signal processor 44. In a further embodiment, optical splitters can be used with a laser beam from the laser generator 41 to obtain two or more laser beams. In another embodiment, there may be two laser generators 41 which are respectively used to generate the laser beam 'a' and the laser beam 'b', and the beam switch 42 is no longer required.

The photo-detector 43 is used to detect reflected light 'c' and 'd' (including specular reflected light and scattering reflected light) from the object 20 which is reflected by the main reflective mirror 15 and collected by the multiple collecting fibers 124, and then convert the intensity of the detected reflected light 'c' and 'd' into corresponding electrical signals, such as voltage signals, for subsequent data processing. The photo-detector 43 in this example is typically a single photo-detector but in other embodiment two or more photo-detectors can be employed to provide redundancy and/or to provide individual photo-detectors for each of the reflected light signals 'c' and 'd'.

The signal processor 44 is also used to collect the converted electrical signals from the photo-detector 43, and calculate the surface roughness of the detected position of the object 20 based on the converted electrical signals generated based on the detected reflected light 'c' and 'd'. The signal processor section 44 can include one or more processors and associated memory to store data as well as software routines and algorithms. The data and results can be stored to create a database of the measured surface roughness for the objects 20.

The result display 45 is used to display the calculated result of the surface roughness of the detected position of the object 20. While this example notes displaying the results, the results can also be stored or communicated to another location for subsequent review. In a further embodiment, the results are compared to some predefined threshold values to determine whether the surface roughness is acceptable for the object. If the surface roughness is within the acceptable range, then the object is acceptable. However, if the surface roughness exceeds the threshold value, the object is rejected.

Figure 5B:
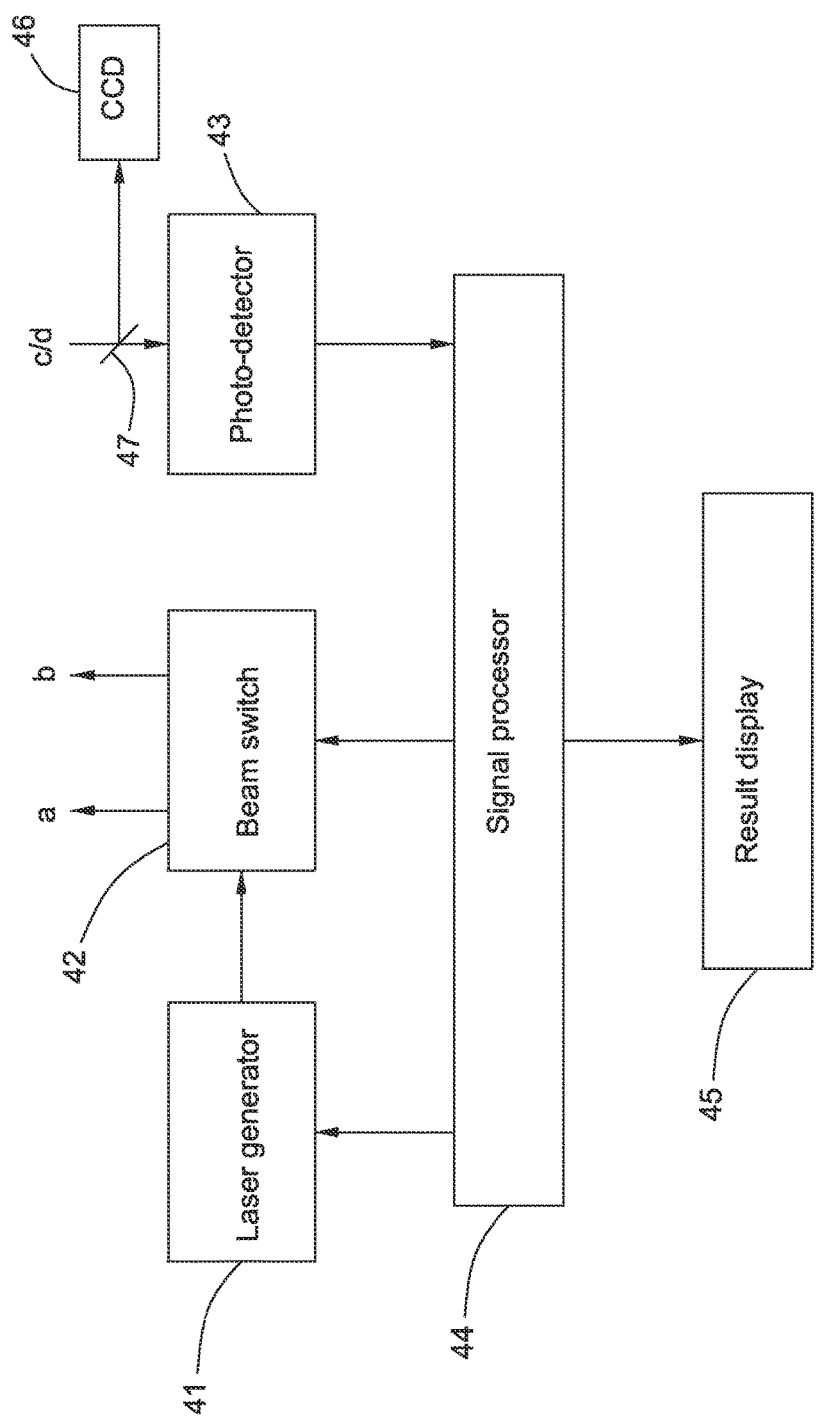
FIG. 5b is a block diagram of the surface roughness measurement device of FIG. 1, according to another embodiment.

Referring to FIG. 5b, a block diagram of the surface roughness measurement device 10 of FIG. 1, according to another embodiment is shown. Compared with the embodiment of FIG. 5a, the surface roughness measurement device 10 of FIG. 5b may further include a charge-coupled device (CCD) 46 and an optical splitter 47. The optical splitter 47 is used to split two transmission channels of the reflected light 'c' and 'd', one transmission channel is used to transmit the reflected light 'c' and 'd' to the photo-detector 43, and the other transmission channel is used to transmit the reflected light 'c' and 'd' to the CCD 46. The CCD 46 is used to directly show the light image of the reflected light 'c' and 'd', which may determine a surface roughness of the object 20. In some embodiments, the photo-detector 43 and the optical splitter 47 are optional and only the CCD 46 is used to measure the surface roughness of the object 20. The CCD 46 also can be replaced by other types of light imaging devices.

Figure 6A:
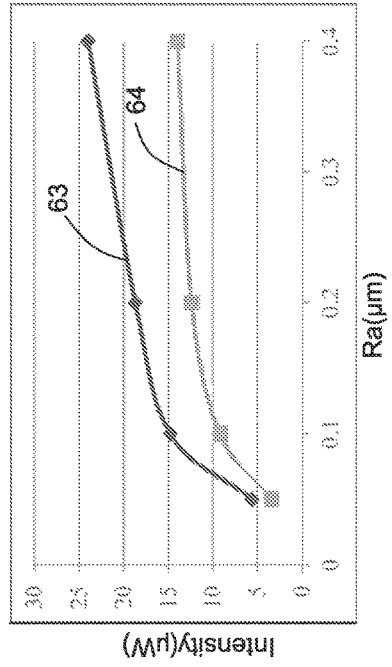
FIG. 6a is a diagram illustrating a comparison of correlations of the roughness of an object and the intensity of the detected reflected light from a main emitting fiber with two different material reflectivities of the object.

Referring to FIG. 6a, a diagram illustrating a comparison of correlations of the roughness of the object 20 and the intensity of the detected reflected light 'c' from the main emitting fiber 122 with two different material reflectivities of the object 20 is shown. The curve 61 corresponds to a first material reflectivity of the object 20, and curve 62 corresponds to a second material reflectivity of the object 20. In other embodiments, the two curves 61 and 62 respectively correspond to two objects 20 that have different material reflectivities. Because the material reflectivities of the two objects 20 are different, the two curves 61 and 62 are also different. In other words, if many objects 20 having different material reflectivities need to be measured, and their roughness is only based on the detected reflected light 'c'. A corresponding number of curves, like curves 61 and 62, need to be processed in advance. Those curves, such as curves 61 and 62 can be processed via appropriate algorithms.

Figure 6B:
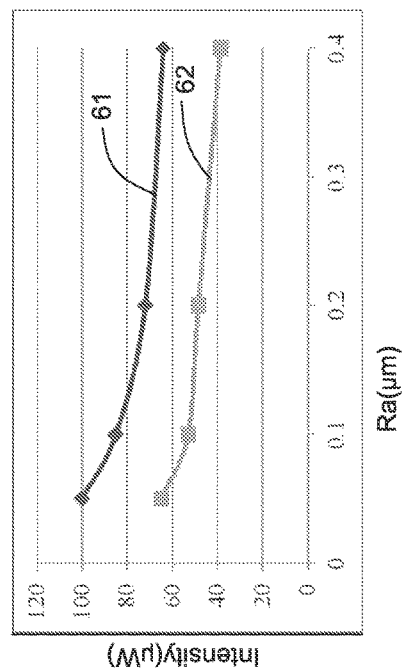
FIG. 6b is a diagram illustrating a comparison of correlations of the roughness of an object and the intensity of the detected reflected light from an auxiliary emitting fiber with two different material reflectivities of the object.

Referring to FIG. 6b, a diagram illustrating a comparison of correlations of the roughness of the object 20 and the intensity of the detected reflected light 'd' from the auxiliary emitting fiber 13 with two different material reflectivities of the object 20 is shown. The curve 63 corresponds to the first material reflectivity of the object 20, and the curve 64 corresponds to the second material reflectivity of the object 20. In other embodiments, the two curves 63 and 64 respectively correspond to two objects that have different material reflectivities. Because the material reflectivities of the two objects 20 are different, the two curves 63 and 64 are also different. In other words, if many objects 20 having different material reflectivities need to be measured, and their roughness is only based on the detected reflected light 'd'. A corresponding number of curves, like curves 63 and 64, need to be calculated in advance. Those curves, such as curves 63 and 64 can be calculated via appropriate algorithms.

Figure 6C:
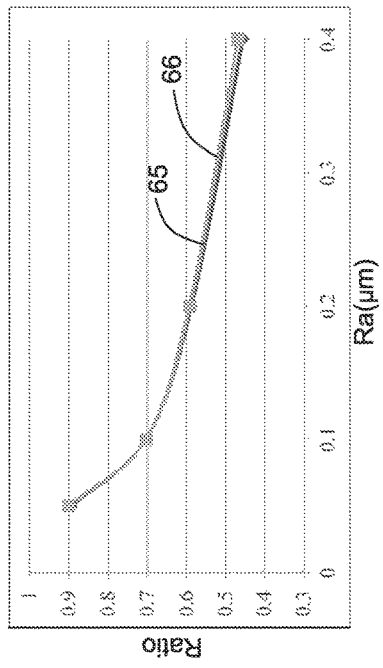
FIG. 6c is a diagram illustrating a comparison of correlations of the roughness of an object and a ratio calculated by the intensity of the detected reflected light from a main emitting fiber and an auxiliary emitting fiber with two different material reflectivities of the object.

Referring to FIG. 6c, a diagram illustrating a comparison of correlations of the roughness of the object 20 and a ratio calculated by the intensity of the detected reflected light 'c' and 'd' from the main and auxiliary emitting fibers 122 and 13 with two different material reflectivities of the object 20 is shown. The ratio is calculated by the material reflectivities of the object 20 and the intensity of the detected reflected light 'c' and 'd'. Namely, a ratio curve 65 is calculated by the curves 61 and 63, and a ratio curve 66 is calculated by the curves 62 and 64. As an example, the ratio is calculated according to the following equation: $R=(kMI-kAI)/(kMI+kAI)=(MI-AI)/(MI+AI)$. Wherein, R is the ratio, k is the material reflectivity, MI is the intensity of the detected reflected light 'c' such as corresponding to the curves 61 and 63, AI is the intensity of the detected reflected light 'd' such as corresponding to the curves 62 and 64. When the object 20 has the first material reflectivity, a corresponding ratio R is calculated based on the above equation, for example the ratio curve 65 is calculated based on the curve 61 and 63 by using the above equation, and the ratio curve 66 is calculated based on the curve 62 and 64 by using the above equation as well.

In the above equation $R=(kMI-kAI)/(kMI+kAI)=(MI-AI)/(MI+AI)$, the material reflectivity parameter k are eliminated, so the ratio curves 65 and 66 are almost the same. Thus, whatever the material reflectivities are, the corresponding ratio curves are the same, and then only one ratio curve (65 or 66) are determined for calculating the roughness of the objects 20, which makes the surface roughness measurement device 10 simple to calibrate and thereby have increased efficiency. For example, a ratio curve 65 is determined in advance, after measuring the roughness of a first object by using the surface roughness measurement device 10, the intensity of the detected reflected light 'c' and 'd' from the main and auxiliary emitting fibers 122 and 13 are calculated by the signal processor 44 respectively, and then the roughness of a first object can be calculated based on the determined ratio curve 65 and the above equation. When a second object is measured by the surface roughness measurement device 10, the roughness of the second object also can be calculated based on the determined ratio curve 65 and the above equation. Namely, only one determined ratio curve 65 is required to calculate roughness of different objects having different material reflectivities. In other words, this surface roughness measurement device 10 can automatically compensate the influence of material reflectivity variation.

Figures 7A, 7B:
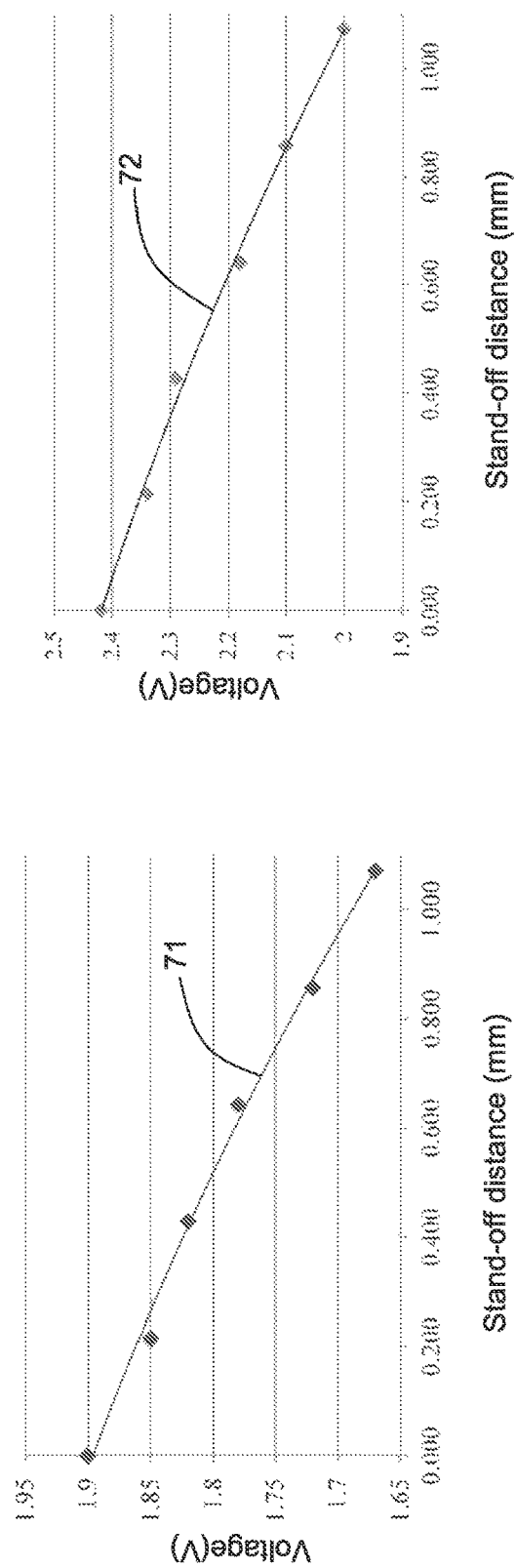
FIG. 7a is a diagram illustrating correlations of the stand-off distance of a surface roughness measurement device and voltage values calculated based on intensity of the detected reflected light from a main emitting fiber.
FIG. 7b is a diagram illustrating correlations of the stand-off distance of a surface roughness measurement device and voltage values calculated based on intensity of the detected reflected light from an auxiliary emitting fiber.

Referring to FIG. 7a, a diagram illustrating correlations of the stand-off distance of the surface roughness measurement device 10 and the voltage values calculated by the photondetector 43 based on the intensity of the detected reflected light from the main emitting fiber 122 is shown. The relationship between the stand-off distance and the voltage values is shown as a curve 71 in FIG. 7a. Obviously, the stand-off distance variation, maybe caused by vibration in the shop, will influence the calculated voltage values. Namely, the stand-off variation will influence measured roughness result when only using the detected reflected light from the main emitting fiber 122. In FIG. 7a, a variation ratio of the curve 71 is about 12%. The term "stand-off distance" is the distance from the aperture 142 of the device 10 to the area of interest of the object 20.

Referring to FIG. 7b, a diagram illustrating correlations of the stand-off distance of the surface roughness measurement device 10 and the voltage values calculated by the photodetector 43 based on the intensity of the detected reflected light from the auxiliary emitting fiber 13 is shown. The relationship between the stand-off distance and the voltage values is shown as a curve 72 in FIG. 7b. Obviously, the stand-off variation will influence the calculated voltage values. Namely, the stand-off variation will influence measured roughness result when only using the detected reflected light from the auxiliary emitting fiber 13. In FIG. 7b, a variation ratio of the curve 72 is about 17%.

Figure 7C:
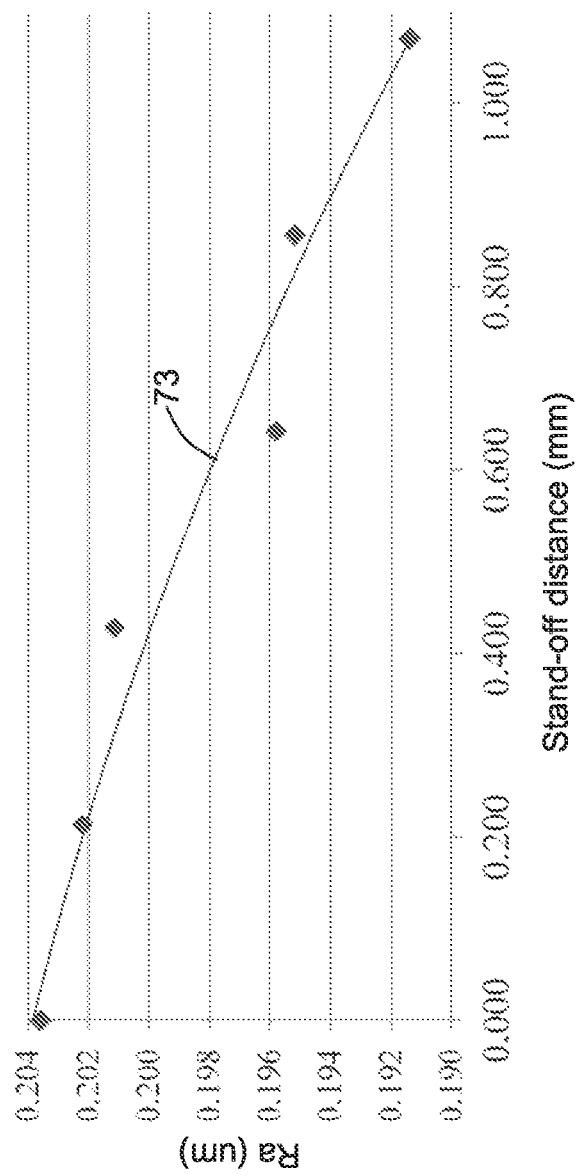
FIG. 7c is a diagram illustrating correlations of the stand-off distance of a surface roughness measurement device and calculated roughness based on the intensity of the detected reflected light from both of a main emitting fiber and an auxiliary emitting fiber.

Referring to FIG. 7c, a diagram illustrating correlations of the stand-off distance of the surface roughness measurement device 10 and the calculated roughness based on the intensity of the detected reflected light from both of the main emitting fiber 122 and the auxiliary emitting fiber 13 is shown. The relationship between the stand-off distance and the calculated roughness is shown as a curve 73 in FIG. 7c. Similarly, the stand-off variation will also influence the calculated roughness, when using both of the detected reflected light from the main emitting fiber 122 and the auxiliary emitting fiber 13. However, the combination of the main emitting fiber 122 and the auxiliary emitting fiber 13 can reduce the stand-off variation influence. In FIG. 7c, a variation ratio of the curve 73 is only about 5% which is less than 12% and 17%. Therefore, the surface roughness measurement device 10 is almost immune to the vibration situation.

Figure 8B:
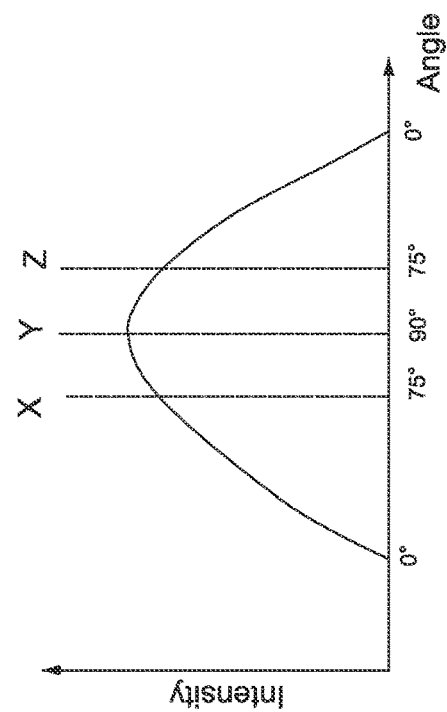
FIG. 8b is a diagram illustrating correlations of the measuring angles of the surface roughness measurement device of FIG. 8a and detected scattering intensity by the surface roughness measurement device.
Figure 8A:
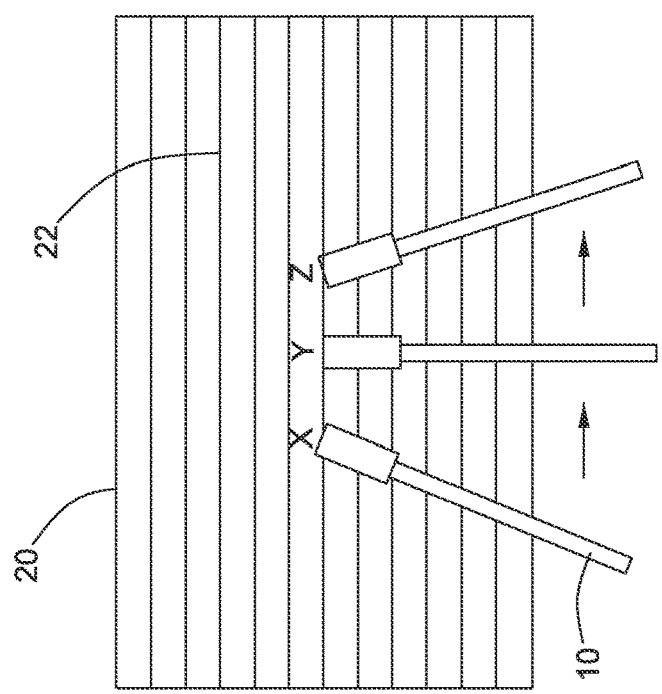
FIG. 8a is a schematic view illustrating three different measuring positions of a surface roughness measurement device.

Referring to FIG. 8a, a schematic view illustrating three different measuring positions X, Y, Z of the surface roughness measurement device 10 is shown. Before measuring an object 20, the direction of the machining mark 22 of the object 20 needs to be determined in advance typically, namely the measuring direction should be perpendicular to the machining mark 22 during the roughness measuring process, such as the measuring position Y is an appropriate measuring position.

Referring to 8b, a diagram illustrating correlations of the measuring angles of the surface roughness measurement device 10 and the detected scattering intensity from the auxiliary emitting fiber 13 by the surface roughness measurement device 10 is shown. It is understood that the scattering intensity from the auxiliary emitting fiber 13 is biggest at the perpendicular measuring position Y. The surface roughness measurement device 10 is rotated on the surface of the object 10, and the result display 45 can show a curve of the scattering intensity at the same time. When the scattering intensity from the auxiliary emitting fiber 13 reaches to the highest value, that means the measuring direction Y of the surface roughness measurement device 10 is now perpendicular to the machining mark 22, and then the surface roughness of the object 20 can be calculated at the measuring position Y accordingly, which obtains a correct roughness measuring value.

Figure 9A:
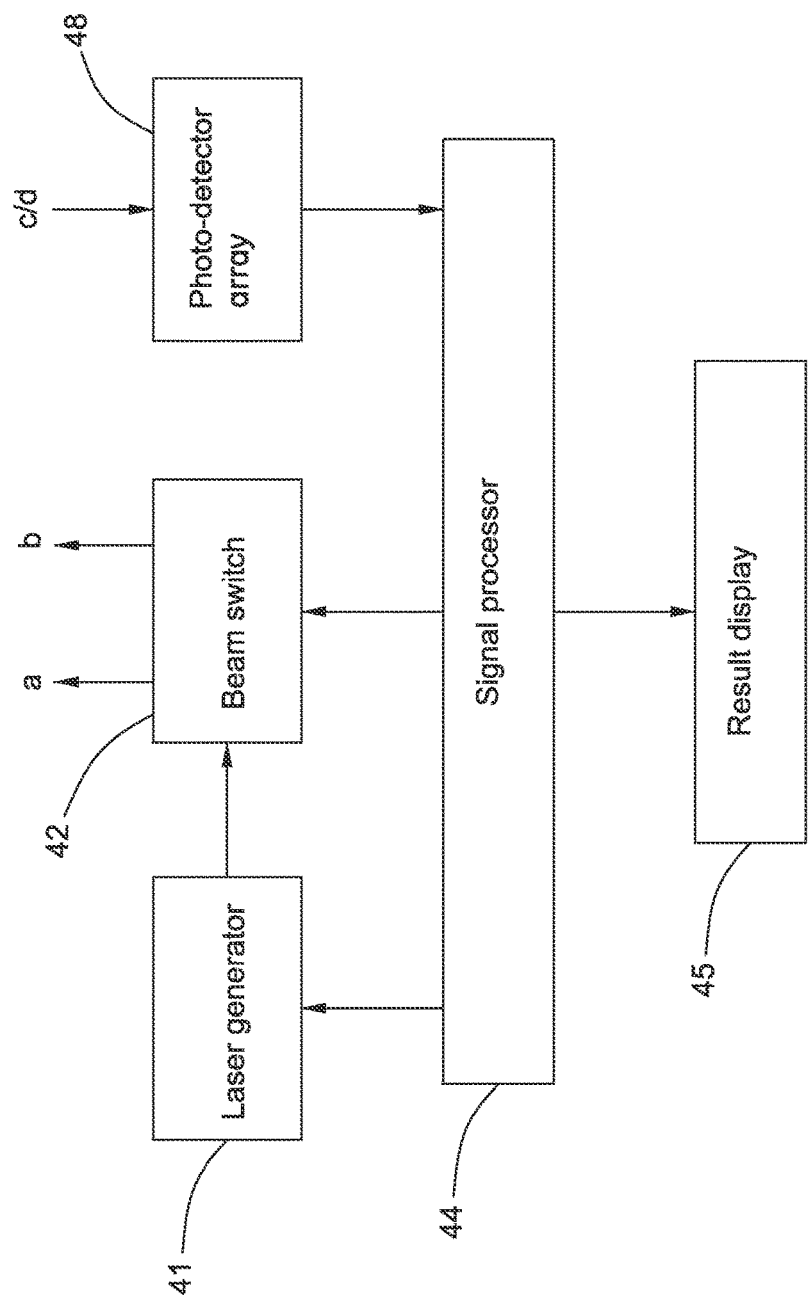
FIG. 9a is a block diagram of the surface roughness measurement device of FIG. 1, according to yet another embodiment.

Referring to FIG. 9a, a block diagram of the surface roughness measurement device 10 of FIG. 1, according to yet another embodiment is shown. Compared with the embodiment of FIG. 5a, the surface roughness measurement device 10 of FIG. 9a applies a photo-detector array 48 to replace the photo-detector 43. In some embodiments, the number of the photo-detectors of the photo-detector array 48 is equal to the number of the collecting fibers 124, and used to respectively detect reflected light from the collecting fibers 124 and then convert the intensity of the detected reflected light into corresponding electrical signals, such as voltage signals, for subsequent data processing.

Figure 9B:
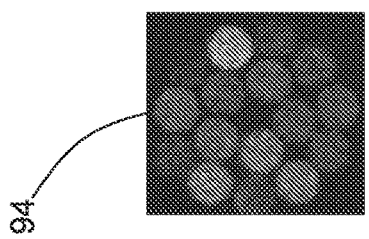
Figure 9B:
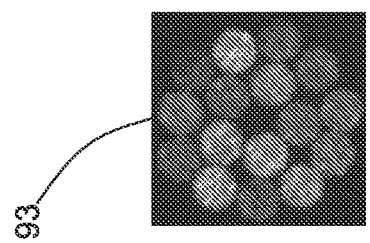
Figure 9B:
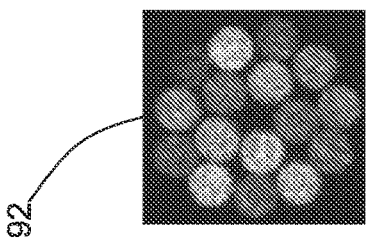
Figure 9B:
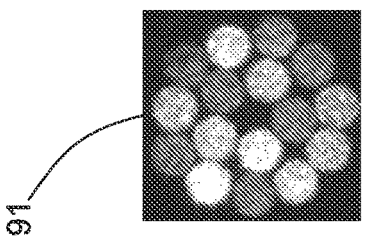

In this example, the signal processor 44 is further used to collect the converted electrical signals from the photo-detectors of photo-detector array 48. The detected signals from the photo-detector array 48 can be processed by the processor 44 to calculate an intensity image based on the converted electrical signals, which can be shown on the result display 45. For example, FIG. 9b shows four intensity images 91, 92, 93, 94 which illustrate the intensity distribution of the collecting fibers 124. For ease of illustrations, each of the intensity images 91, 92, 93, 94 only shows a part of the intensity distribution of the collecting fibers 124. As the example, the intensity of the intensity images 91, 92, 93, 94 are gradually reduced. Namely, the surface roughness values of the object 20 corresponding to the intensity images 91, 92, 93, 94 are gradually increased. Some reference images corresponding to different surface roughness values can be determined in advance. Then, users can determine a rough roughness of the object 20 by comparing the calculated intensity image with the predetermined reference images. In other embodiments, the photo-detector array 48 also can act as the photo-detector 45 to calculate the surface roughness.

In another embodiment, historical data of the surface roughness of an object can be compared in time to show the change in surface roughness. By comparing the baseline data with subsequent surface roughness data, diagnostic and prognostic analysis can be implemented.

Figure 10:
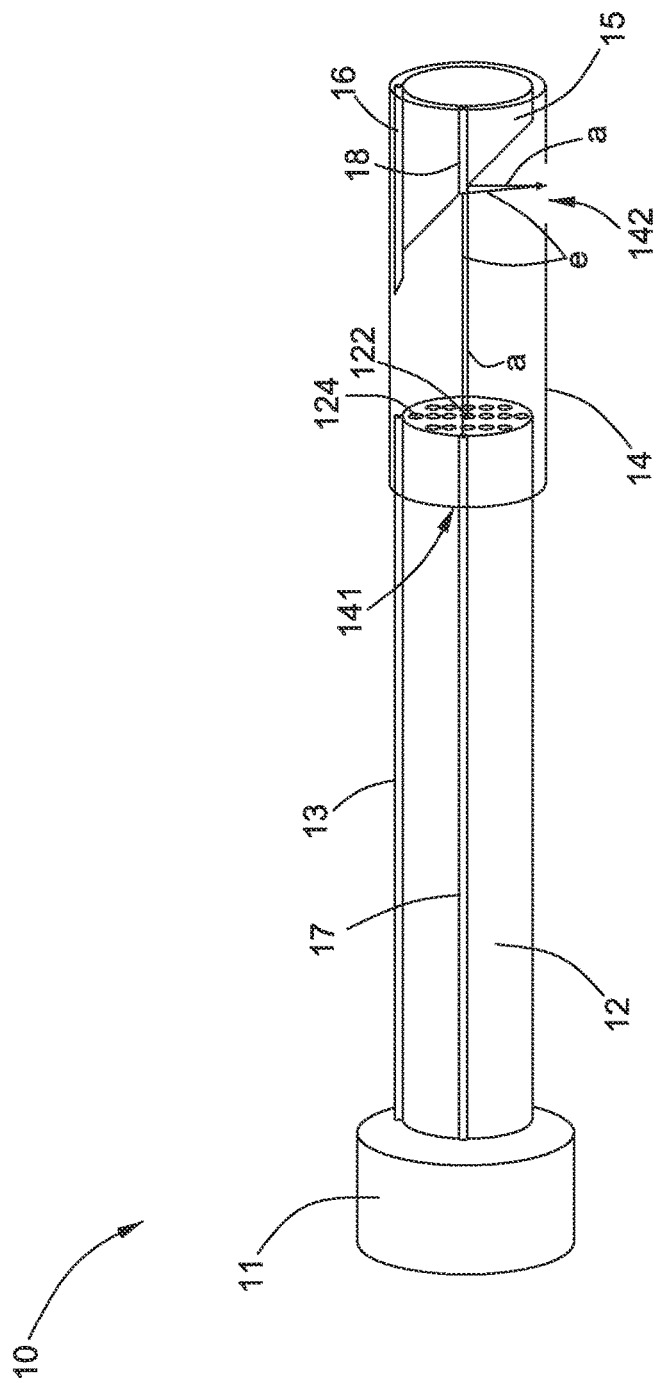
FIG. 10 is a schematic, perspective view of a surface roughness measurement device, according to another embodiment.

Referring to FIG. 10, a schematic, perspective view of a surface roughness measurement device 10, according to another embodiment is shown. Compared with FIG. 1, the roughness measurement device 10 of FIG. 10 further includes another auxiliary emitting fiber 17 and another miniature auxiliary reflective mirror 18. Correspondingly, the beam switch 42 will provide three switch channels for the main emitting fiber 122, the auxiliary emitting fiber 13, and the auxiliary emitting fiber 17 respectively (now shown).

The auxiliary emitting fiber 17 is arranged proximate the fiber bundle 12 and has the same emitting direction as the main emitting fiber 122. The auxiliary reflective mirror 18 is arranged in the optical housing 14. Compared with the auxiliary emitting fiber 13, the auxiliary emitting fiber 17 is arranged with a 90 degrees direction, and the auxiliary reflective mirror 18 is correspondingly arranged with a 90 degrees direction compared with the auxiliary reflective mirror 16. Furthermore, the arrangement of the auxiliary reflective mirror 18 also should satisfy that when a laser beam 'e' is emitted from the auxiliary emitting fiber 17 to the auxiliary reflective mirror 18, the reflected laser beam 'e' reflected by the auxiliary reflective mirror 18 will intersect with the reflected laser beam 'a' reflected by the main reflective mirror 15 at the same detecting point of the aperture 142. Namely, when the object 20 is proximate the aperture 142, the reflected laser beams 'a' and 'e' are respectively transmitted to a same detecting point at the measuring surface of the object 20. Furthermore, a plane formed by the reflected laser beam 'e' and 'a' is roughly perpendicular to a plane formed by the reflected laser beam 'b' and 'a'. The gradient angle of the auxiliary reflective mirror 18 can be changed according to the real position arrangement of the auxiliary reflective mirror 18 in the optical housing 14 in different embodiments.

Similarly, based on the reflected laser beams 'a' and 'e', a surface roughness of the object 20 also can be calculated according to above mentioned calculation method. Due to the size requirements and shape of the surface roughness measurement device 10, it may not be able to be rotated in a difficult access area, such as in a narrow hole. In such a situation, the surface roughness measurement device 10 may not be able to measure the direction of machining mark 22 of the object 20 as mentioned for FIGS. 8a and 8b. In this scenario, the surface roughness of the object 20 is calculated based on the reflected laser beams 'a' and 'b', and calculated based on the reflected laser beams 'a' and 'e' as well. After two surface roughness values of the object 20 are calculated, the greater of the two surface roughness values is determined as the real surface roughness, which can increase measurement accuracy. In other embodiments, the roughness measurement device 10 may include more than one auxiliary emitting fiber 17 and auxiliary reflective mirror 18, which can calculate more than two surface roughness values to further increase measurement accuracy.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

The invention claimed is:

1. A surface roughness measurement device, the surface roughness measurement device comprising:
   a fiber bundle comprising a main emitting fiber and a plurality of collecting fibers;
   a first auxiliary emitting fiber;
   an optical housing comprising the fiber bundle and the first auxiliary emitting fiber and defining an aperture for optically contacting a surface of an object;
   a main reflective mirror arranged in the optical housing, for reflecting light emitted from the main emitting fiber to a detecting point of the aperture and reflecting light reflected by the object to the plurality of collecting fibers;
   a first auxiliary reflective mirror arranged in the optical housing, for reflecting light emitted from the first auxiliary emitting fiber to the detecting point of the aperture; and
   an external circuit for generating a laser beam to the main emitting fiber and the first auxiliary emitting fiber, collecting the reflected light from the plurality of collecting fibers, and calculating the surface roughness of the object based on the collected reflected light,
   wherein the surface roughness of the object is calculated based on a predetermined relationship between the surface roughness and a ratio of the intensity of a detected reflected light based on light emitted from the main emitting fiber and intensity of the detected reflected light based on the light emitted from the first auxiliary emitting fiber, and
   wherein the ratio is calculated by an equation $R=(MI-AI)/(MI+AI)$, wherein R is the ratio, MI is the intensity of the detected reflected light based on the light emitted from the main emitting fiber, AI is the intensity of the detected reflected light based on the light emitted from the first auxiliary emitting fiber.

2. The surface roughness measurement device of claim 1, wherein the external circuit comprises:
   a laser generator for generating the laser beam;
   a photo-detector for detecting the reflected light collected from the plurality of collecting fibers and converting the collected light into electrical signals; and
   at least one signal processor for calculating the surface roughness of the object based on the converted electrical signals converted from the reflected light from the main emitting fiber and converted from the reflected light from the first auxiliary emitting fiber.

3. The surface roughness measurement device of claim 2, wherein the external circuit further comprises a beam switch for selectively switching the laser beam to the main emitting fiber and the first auxiliary emitting fiber.

4. The surface roughness measurement device of claim 2, wherein the external circuit further comprises:
   a charge-coupled device (CCD); and
   an optical splitter for splitting the reflected light collected from the plurality of collecting fibers to the photo-detector and the CCD respectively.

5. The surface roughness measurement device of claim 1, wherein the main emitting fiber is arranged about the center of the plurality of collecting fibers in the fiber bundle.

6. The surface roughness measurement device of claim 1, wherein the optical housing defines an opening at one end thereof, a distal end of the fiber bundle with the first auxiliary emitting fiber is retained in at least part of the optical housing through the opening.

7. The surface roughness measurement device of claim 6, wherein the main reflective mirror is arranged in the optical housing and positioned with respect to the fiber bundle with 45 degrees.

8. The surface roughness measurement device of claim 7, wherein the first auxiliary reflective mirror is arranged in the optical housing and positioned with respect to the first auxiliary emitting fiber with a gradient angle which is less than 45 degrees, the distance between the first auxiliary emitting fiber and the first auxiliary reflective mirror is less than the distance between the fiber bundle and the main reflective mirror.

9. The surface roughness measurement device of claim 1, wherein the external circuit comprises:
   a laser generator for generating the laser beam;
   a photo-detector array comprising a plurality of photo-detectors for respectively detecting the reflected light collected from the plurality of collecting fibers and converting the collected light into electrical signals; and
   a signal processor for showing an intensity distribution image of the detected reflected light based on the converted electrical signals through a display.

10. The surface roughness measurement device of claim 1, further comprising:
    a second auxiliary emitting fiber retained in the optical housing; and
    a second auxiliary reflective mirror arranged in the optical housing, for reflecting light emitted from the second auxiliary emitting fiber to the detecting point of the aperture;
    wherein the external circuit is further for providing the laser beam to the second auxiliary emitting fiber.

11. The surface roughness measurement device of claim 10, wherein the surface roughness of the object is calculated based on a predetermined relationship between the surface roughness and a ratio of the intensity of the detected reflected light based on the light emitted from the main emitting fiber and the intensity of the detected reflected light based on the light emitted from one of the first auxiliary emitting fiber and the second auxiliary emitting fiber.

12. The surface roughness measurement device of claim 11, wherein the ratio is calculated by an equation $R=(MI-AI)/(MI+AI)$, wherein R is the ratio, MI is the intensity of the detected reflected light based on the light emitted from the main emitting fiber, AI is the intensity of the detected reflected light based on the light emitted from the first auxiliary emitting fiber or the second auxiliary emitting fiber.

13. The surface roughness measurement device of claim 10, wherein a plane formed by the reflected laser beam of the main reflective mirror and the reflected laser beam of the first auxiliary emitting fiber is perpendicular to a plane formed by the reflected laser beam of the main reflective mirror and the reflected laser beam of the second auxiliary emitting fiber.

14. The surface roughness measurement device of claim 13, wherein the second auxiliary emitting fiber is arranged with a 90 degrees direction compared with the first auxiliary emitting fiber.

15. The surface roughness measurement device of claim 10, wherein the external circuit further comprises a beam switch for selectively switching the laser beam to the main emitting fiber, the first auxiliary emitting fiber, and the second auxiliary emitting fiber.

16. The surface roughness measurement device of claim 1, wherein the main emitting fiber is arranged about the center of the plurality of collecting fibers in the fiber bundle.

17. The surface roughness measurement device of claim 1, wherein the optical housing defines an opening at one end thereof, a distal end of the fiber bundle with the first auxiliary emitting fiber is retained in at least part of the optical housing through the opening.

18. The surface roughness measurement device of claim 1, further comprising:
a second auxiliary emitting fiber retained in the optical housing; and
a second auxiliary reflective mirror arranged in the optical housing, for reflecting light emitted from the second auxiliary emitting fiber to the detecting point of the aperture;
wherein the external circuit is further for providing the laser beam to the second auxiliary emitting fiber.

19. A surface roughness measurement device, the surface roughness measurement device comprising:
a fiber bundle comprising a main emitting fiber and a plurality of collecting fibers;
a plurality of auxiliary emitting fibers;
an optical housing comprising the fiber bundle and the plurality of auxiliary emitting fibers and defining an aperture for optically contacting a surface of an object;
a main reflective mirror arranged in the optical housing, for reflecting light emitted from the main emitting fiber to a detecting point of the aperture and reflecting light reflected by the object to the plurality of collecting fibers;
a plurality of auxiliary reflective mirrors arranged in the optical housing, for respectively reflecting light emitted from the plurality of auxiliary emitting fibers to the detecting point of the aperture; and
an external circuit for generating a laser beam to the main emitting fiber and the plurality of auxiliary emitting fibers, collecting the reflected light from the plurality of collecting fibers, and calculating the surface roughness of the object based on the collected reflected light,
wherein the surface roughness of the object is calculated based on a predetermined relationship between the surface roughness and a ratio of the intensity of detected reflected light based on light emitted from the main emitting fiber and the intensity of the detected reflected light based on the light emitted from one of the plurality of auxiliary emitting fibers, and
wherein the ratio is calculated by an equation $R=(MI-AI)/(MI+AI)$, wherein R is the ratio, MI is the intensity of the detected reflected light based on the light emitted from the main emitting fiber, AI is the intensity of the detected reflected light based on the light emitted from one of the plurality of auxiliary emitting fibers.

20. The surface roughness measurement device of claim 19, wherein the external circuit comprises:
a laser generator for generating the laser beam;
a photo-detector for detecting the reflected light collected from the plurality of collecting fibers and converting the collected light into electrical signals; and
at least one signal processor for calculating the surface roughness of the object based on the converted electrical signals converted from the reflected light from the main emitting fiber and converted from the reflected light from the first auxiliary emitting fiber.

* * * * *